US010311176B2

(12) United States Patent
Ohnishi et al.

(10) Patent No.: US 10,311,176 B2
(45) Date of Patent: Jun. 4, 2019

(54) SIMULATION METHOD, SIMULATION APPARATUS, AND SIMULATION PROGRAM

(71) Applicant: Sumitomo Heavy Industries, Ltd., Tokyo (JP)

(72) Inventors: Yoshitaka Ohnishi, Kanagawa (JP); Daiji Ichishima, Kanagawa (JP); Shuji Miyazaki, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 291 days.

(21) Appl. No.: 15/244,809

(22) Filed: Aug. 23, 2016

(65) Prior Publication Data

US 2017/0068759 A1  Mar. 9, 2017

(30) Foreign Application Priority Data

Sep. 3, 2015 (JP) ................................ 2015-173647
Feb. 2, 2016 (JP) ................................ 2016-017588

(51) Int. Cl.
*G06F 17/13* (2006.01)
*G06F 17/50* (2006.01)

(52) U.S. Cl.
CPC .......... *G06F 17/5009* (2013.01); *G06F 17/13* (2013.01); *G06F 2217/16* (2013.01); *G06F 2217/80* (2013.01)

(58) Field of Classification Search
CPC .. G06F 17/5009; G06F 17/13; G06F 2217/80; G06F 2217/16

USPC ............................................................ 703/2
See application file for complete search history.

(56) References Cited

U.S. PATENT DOCUMENTS 6,915,245 B1 * 7/2005 Hinton ................ G06F 17/5009
702/50

FOREIGN PATENT DOCUMENTS

| EP | 2899655 A1 | 7/2015 |
| JP | 5441422 B2 | 3/2014 |

OTHER PUBLICATIONS

Bitzek et al.: "Structural Relaxation Made Simple," Physical Review Letters, XP055355986, ISSN: 0031-9007, DOI: 10.1103/PhysRevLett. 97.170201, vol. 97, No. 17, Oct. 1, 2006.

(Continued)

*Primary Examiner* — Saif A Alhija
(74) *Attorney, Agent, or Firm* — Michael Best & Friedrich LLP

(57) ABSTRACT

A coupled simulation of a structural-elastic phenomenon and a heat conduction phenomenon of a simulation target including plural particles is performed. Here, numerical calculation of a motion equation capable of being transformed into an equation of the same form as that of a heat conduction equation is performed with respect to a term of a spatial temperature distribution and a term of a derivative of temperature with respect to time, to perform a simulation of the heat conduction phenomenon of the simulation target.

9 Claims, 13 Drawing Sheets

(56) References Cited

OTHER PUBLICATIONS

Monaghan: "Smoothed particle hydrodynamics; Smoothed particle hydrodynamics," Reports on Progress in Physics, Institute of Physics Publishing, XP020084661, ISSN: 0034-4885, DOI: 10.1088/0034-4885/68/8/RO1, vol. 68, No. 8, Aug. 1, 2005.
Zengyuan et al: "Molecular Dynamics Simulation of Heat Propagation in Liquid Argon," Tsinghua Science and Technology, Tsinghua University Press, Beijing, CN, XP011376293, ISSN: 1007-0214, DOI: 103.1109/TST.1997.6078062, vol. 2, No. 2, pp. 613-618, Jun. 1, 1997.
European Search Report issued in Application No. 16183411.4, dated Mar. 30, 2017.

* cited by examiner

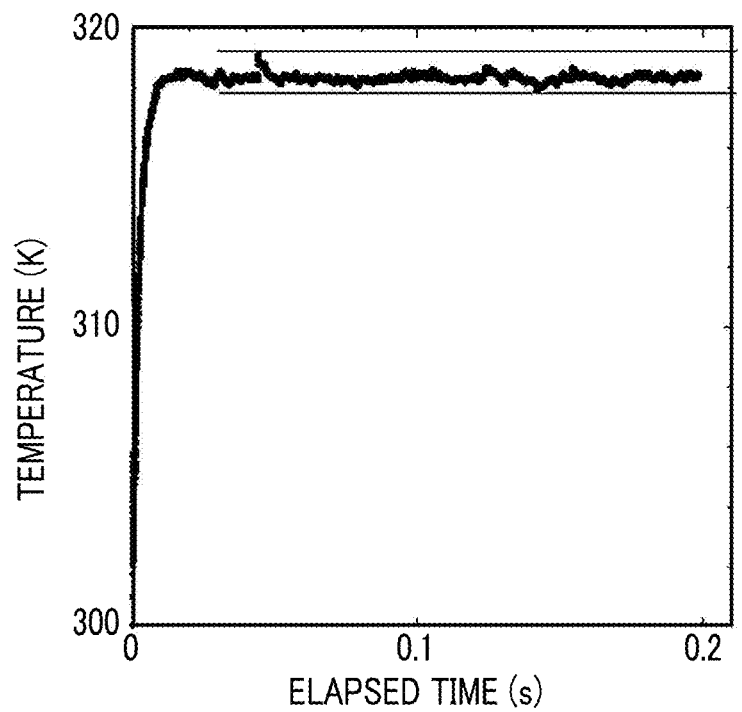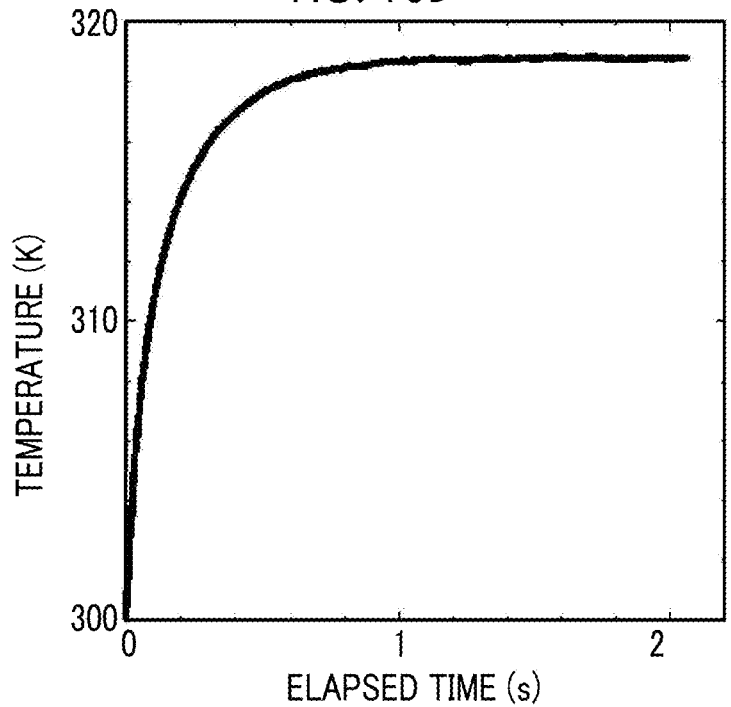

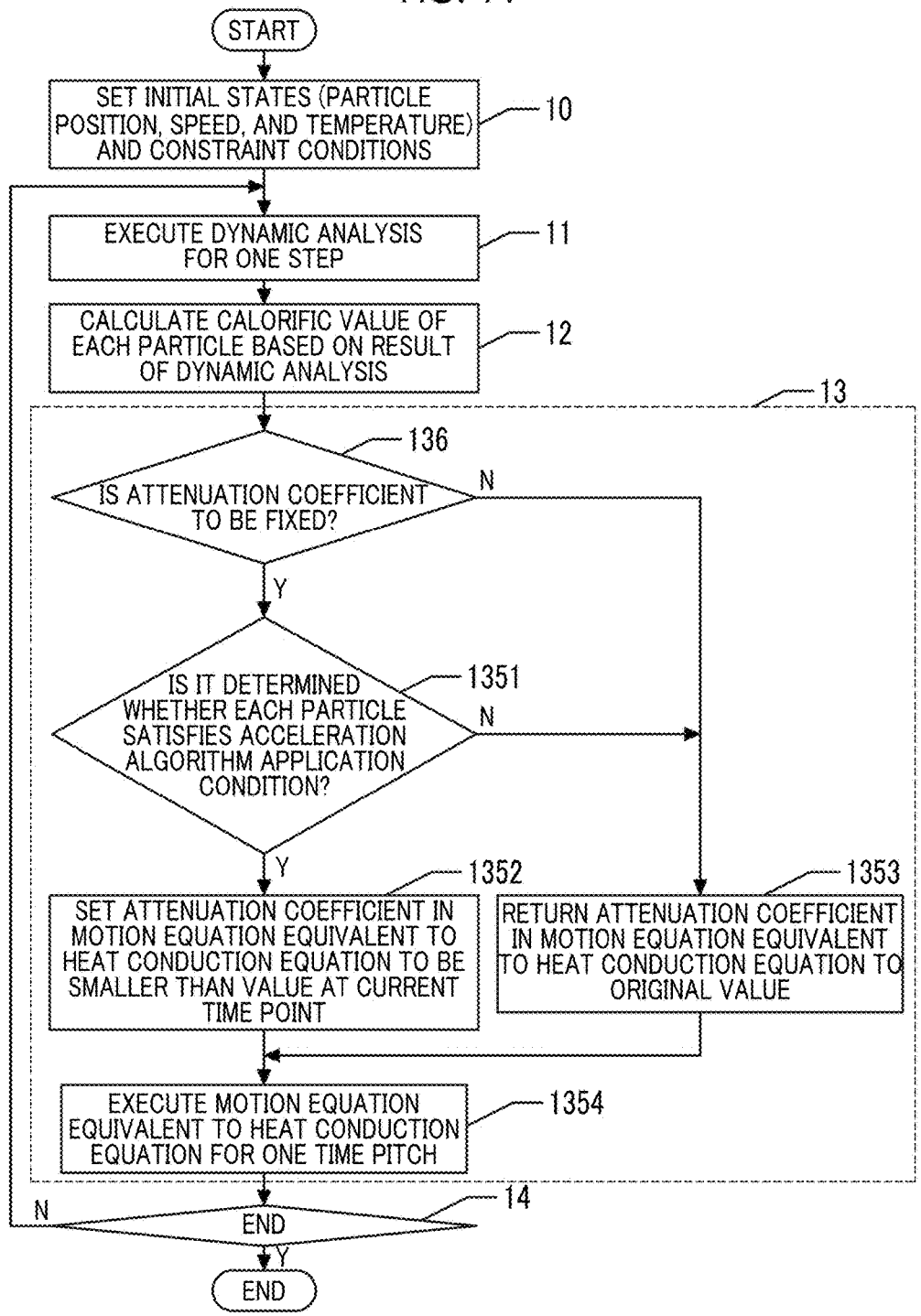

SIMULATION METHOD, SIMULATION APPARATUS, AND SIMULATION PROGRAM

RELATED APPLICATIONS

Priority is claimed to Japanese Patent Application Nos. 2016-017588, filed Feb. 2, 2016, and 2015-173647, filed Sep. 3, 2015 the entire content of each of which is incorporated herein by reference.

BACKGROUND

Technical Field

Certain embodiments of the present invention relate to a simulation method, a simulation apparatus, and a simulation program capable of simulating a heat conduction phenomenon of a simulation target.

Description of Related Art

A simulation method based on a molecular dynamics method (MD method) is known as a method for researching phenomena of materials science in general by using computers on the basis of classical mechanics, quantum mechanics, or the like. A renormalization group molecular dynamics method (RMD method) which is a technique developed from the MD method in order to handle a macro scale system has been proposed. With respect to a heat conduction phenomenon of a simulation target, in the MD method or the RMD method, normally, only heat conduction based on lattice vibration (phonons) can be handled. For this reason, if a heat conduction phenomenon of metal in which free electrons greatly contribute to the heat conduction phenomenon is simulated using the MD method or the RMD method, in many cases, results far from an actual phenomenon may be obtained.

In the related art, a simulation method capable of correctly handling a heat conduction phenomenon using the MD method or the RMD method has been proposed. In such a simulation method, temperature parameters are given to particles. By solving a heat conduction equation based on a temperature of each particle at a certain time point, a temperature of each particle at the next time point is calculated. By solving the heat conduction equation, it is possible to perform a simulation in which specific heat and a thermal conductivity of an actual simulation target are considered.

SUMMARY

According to an embodiment of the present invention, there is provided a method of performing a coupled simulation of a structural-elastic phenomenon and a heat conduction phenomenon of a simulation target including a plurality of particles, including: performing numerical calculation of a motion equation capable of being transformed into an equation of the same form as that of a heat conduction equation with respect to a term of a spatial temperature distribution and a term of a derivative of temperature with respect to time to perform a simulation of the heat conduction phenomenon of the simulation target.

According to another embodiment of the present invention, there is provided a simulation apparatus that performs a coupled simulation of a structural-elastic phenomenon and a heat conduction phenomenon of a simulation target including a plurality of particles, including: a storage unit that stores a motion equation capable of being transformed into an equation of the same form as that of a heat conduction equation with respect to a term of a spatial temperature distribution and a term of a derivative of temperature; a central processing unit that performs numerical calculation of the motion equation stored in the storage unit to calculate a temperature distribution of the simulation target; and an output unit that outputs a result of the numerical calculation performed by the central processing unit.

According to still another embodiment of the present invention, there is provided a simulation program that causes a computer to execute a coupled simulation of a structural-elastic phenomenon and a heat conduction phenomenon of a simulation target including a plurality of particles, in which the simulation program realizes a function of performing numerical calculation of a motion equation capable of being transformed into an equation of the same form as that of a heat conduction equation with respect to a term of a spatial temperature distribution and a term of a derivative of temperature with respect to time to perform a simulation of the heat conduction phenomenon of the simulation target.

BRIEF DESCRIPTION OF THE DRAWINGS

FIG. 10A is a graph illustrating change in the overall temperature calculated using the simulation method according to the reference example in FIG. 9, and FIG. 10B is a graph illustrating change in the overall temperature calculated when an attenuation coefficient is fixed to an original value to perform a simulation.

FIG. 11 is a flowchart illustrating a simulation method according to another embodiment.

DETAILED DESCRIPTION

Generally, temperature change due to a heat conduction phenomenon is smoother than change in particle positions due to a structural phenomenon or an elastic phenomenon (hereinafter, referred to as a "structural-elastic phenomenon"). A time pitch when a heat conduction phenomenon is simulated is set to be longer than a time pitch when a structural-elastic phenomenon is simulated. However, in a coupled simulation for handling both of a heat conduction phenomenon and a structural-elastic phenomenon, the heat conduction phenomenon may also be simulated with a short time pitch for simulating the structural-elastic phenomenon.

In analysis in a temperature field, generally, a temperature distribution in a steady state is attracting interest. If the heat conduction phenomenon is simulated with a short time pitch until the temperature distribution reaches a steady state, the calculation time is lengthened.

It is desirable to provide a simulation method capable of preventing a calculation time for handling a heat conduction phenomenon from being lengthened. Further, it is desirable to provide a simulation apparatus capable of preventing the calculation time from being lengthened. Furthermore, it is desirable to provide a simulation program capable of preventing the calculation time from being lengthened.

Figure 1:
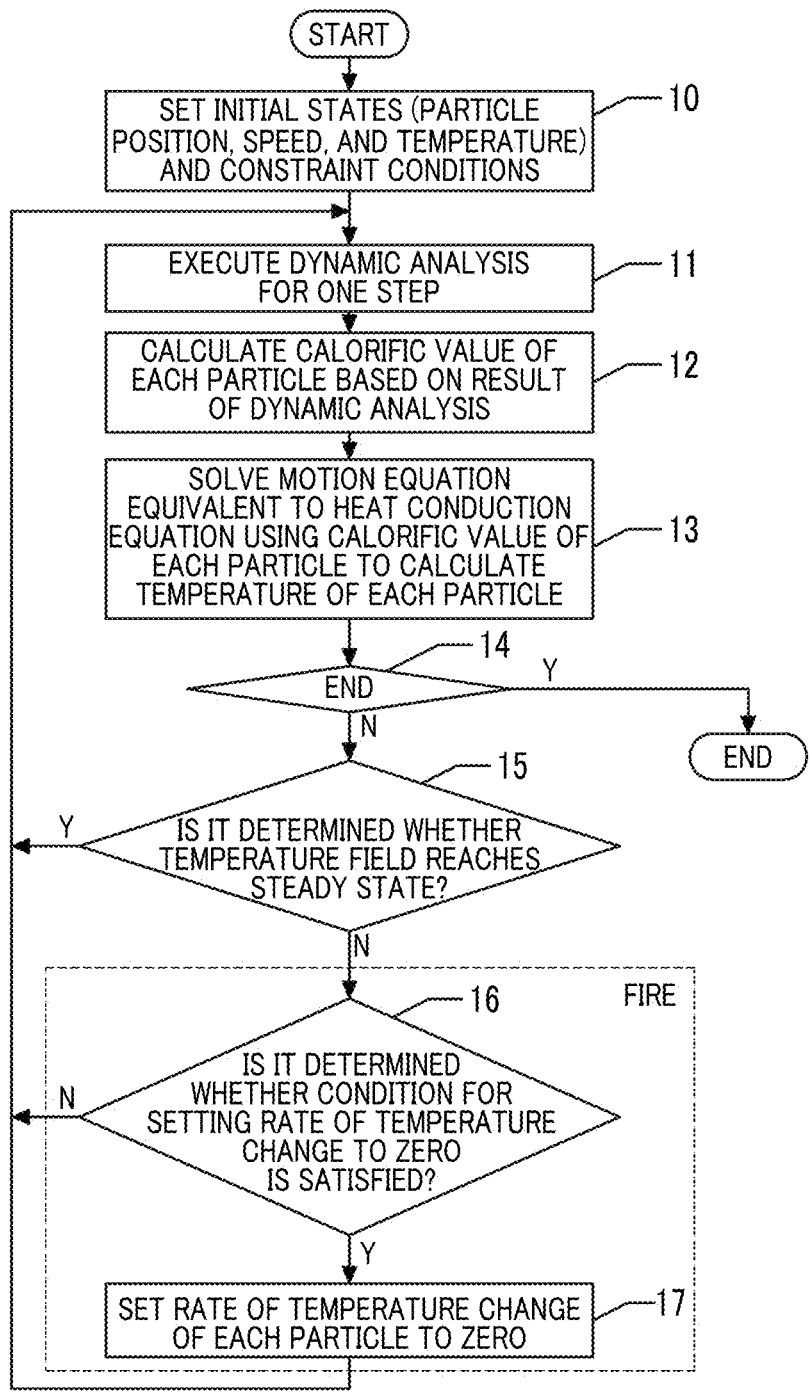
FIG. 1 is a flowchart illustrating a simulation method according to an embodiment.

FIG. 1 shows a flowchart of a simulation method according to an embodiment. In this embodiment, a coupled simulation of a structural-elastic phenomenon and a heat conduction phenomenon of a simulation target that includes plural particles is performed. In the simulation of the structural-elastic phenomenon, a simulation target is expressed as a collection of particles, and dynamic analysis of each particle is performed with a certain time pitch $\Delta t$. Particle methods such as a molecular dynamics (MD) method, a smoothed particle hydrodynamics (SPH) method, a moving particle simulation (MPS) method or a distinct element method (DEM) may be applied to the dynamic analysis. If each particle is considered as a node of a mesh, a finite element method (FEM) may be applied.

In a simulation of the heat conduction phenomenon, temperature parameters are given to respective particles, and calculation of numerical values of temperatures is performed with the same time pitch $\Delta t$ as that in the dynamic analysis. When the calculation of the numerical values of the temperatures is performed, by solving a motion equation equivalent to a heat conduction equation instated of solving the heat conduction equation, analysis of a temperature field is performed. Here, the "equivalent" means that the motion equation can be transformed into an equation of the same form of the heat conduction equation with respect to a term of a spatial temperature distribution and a term of a derivative of temperature with respect to time of the thermal conduction equation. If the position of a mass point in the motion equation corresponds to "temperature", a gradient of a temporal change of a temperature (first-order derivative of the temperature) corresponds to a speed in the motion equation. In this specification, the gradient of the temporal change of the temperature is referred to as a "rate of temperature change".

In analysis of the temperature field, by setting a time constant of a temperature change to be variable, a sloe of the temperature change becomes steeper than a gradient of an actual temperature change. Thus, it is possible to reduce a time until a calculation result with respect to the temperature reaches a steady state. Here, the "steady state" means that the rate of temperature change at a position of each particle is zero.

If the gradient of the temperature change is made steep in the simulation, a temperature obtained in the simulation is overshot, so that a vibration waveform may appear. In this embodiment, by applying a method for relaxing the vibration in a short time, the reduction of the time until the temperature field reaches the steady state is achieved. As the method for relaxing the vibration in a short time, for example, a method called a fast inertial relaxation engine (FIRE) may be applied. The FIRE method is disclosed in ErikBitzek, Pekka Koskinen, Franz Gahler, Michael Moseler, and Peter Gumbsch, "Structural Relaxation Made Simple", Physical Review Letters, 97, 170201 (2006).

Referring to FIG. 1, the simulation method according to this embodiment will be described. In step 10, initial conditions when performing a simulation, such as a position, a speed, a temperature (a temperature of an object at a position of a particle) or the like of each particle that forms a simulation target, and constraint conditions (boundary conditions) therefor are set.

In step 11, dynamic analysis of each particle is executed for only one time pitch. For example, by numerically solving a motion equation of each particle, the position and speed of the particle after a time pitch $\Delta t$ are calculated. In step 12, a calorific value is calculated based on the result of the dynamic analysis. The calorific value P is calculated using the following expression in a contact portion against a different member.

$$P = \mu |F \cdot vr|$$

Here, $\mu$ represents a frictional coefficient, F represents a force applied to the contact portion, and vr represents a relative speed.

In step 13, by solving the motion equation equivalent to the heat conduction equation using the calorific value of each particle, a temperature of each particle after the time pitch $\Delta t$ is calculated.

Figure 2:
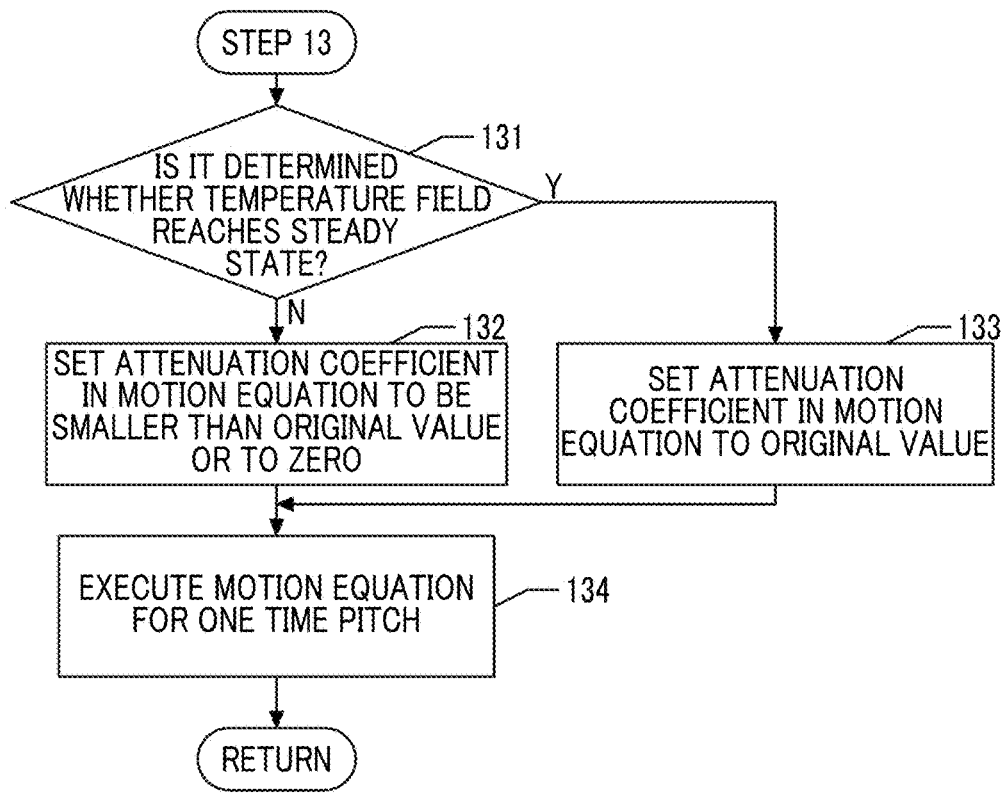
FIG. 2 is a detailed flowchart illustrating step 13 of the flowchart shown in FIG. 1.

FIG. 2 shows a detailed flowchart of step 13. First, in step 131, it is determined whether the calculation result of the temperature field reaches the steady state. The determination of whether the calculation result of the temperature field reaches the steady state is performed by comparing a variation of a calculation value of a temperature of each particle with a determination threshold value. In a case where variations of calculation values of temperatures of all particles are equal to or lower than the threshold value, it is determined that the temperature field reaches the steady state.

In a case where the temperature field does not reach the steady state, in step 132, a parameter (attenuation coefficient) for regulating an attenuation term of the motion equation equivalent to the heat conduction equation is set to be smaller than an original value, or is set to be zero. Until the temperature field reaches the steady state, the motion equation is solved by setting the attenuation coefficient of the motion equation to be smaller than the original value or to be zero. Thus, it is possible to make the temperature change steeper than an original change.

In a case where the temperature field reaches the steady state, in step 133, the attenuation coefficient of the motion equation equivalent to the heat conduction equation becomes equal to the original value. The original value of the attenuation coefficient is determined based on a product of a density of a simulation target and a specific heat thereof, as described in detail later.

After step 132 or step 133, in step 134, numerical calculation of the motion equation equivalent to the heat conduction equation is executed for one time pitch. Here, a value set in step 132 or step 133 is used as the attenuation coefficient of the motion equation. After step 132, the procedure returns to the flowchart of FIG. 1.

In step 14 of FIG. 1, it is determined whether a simulation termination condition is satisfied. As the simulation termination condition, the number of steps of execution of dynamic analysis, or the like may be used, for example. In a case where the simulation termination condition is satisfied, the simulation is terminated. In a case where the simulation termination condition is not satisfied, it is determined in step 15 whether the temperature field reaches the steady state.

In step 15, for example, if the rate of temperature change of each particle becomes equal to or lower than a reference value, it is determined that the temperature field reaches the steady state. In a case where it is determined that the temperature field reaches the steady state, the procedure returns to step 11, and the dynamic analysis is executed for the next one time pitch. In a case where it is determined that the temperature field does not reach the steady state, in step 16, it is determined whether a condition for setting the rate of temperature change to zero is satisfied. This determination is performed for each time pitch of the numerical calculation of the motion equation equivalent to the heat conduction equation.

In step 16, in a case where the determination condition is not satisfied, the procedure returns to step 11, and the dynamic analysis is executed for one time pitch. In step 16, in a case where it is determined that the determination condition is satisfied, in step 17, the rate of temperature change of each particle is set to be zero. Then, the procedure returns to step 11, and then, the dynamic analysis is executed for one time pitch. The technique of step 16 and step 17 is referred to as FIRE.

Figure 3:
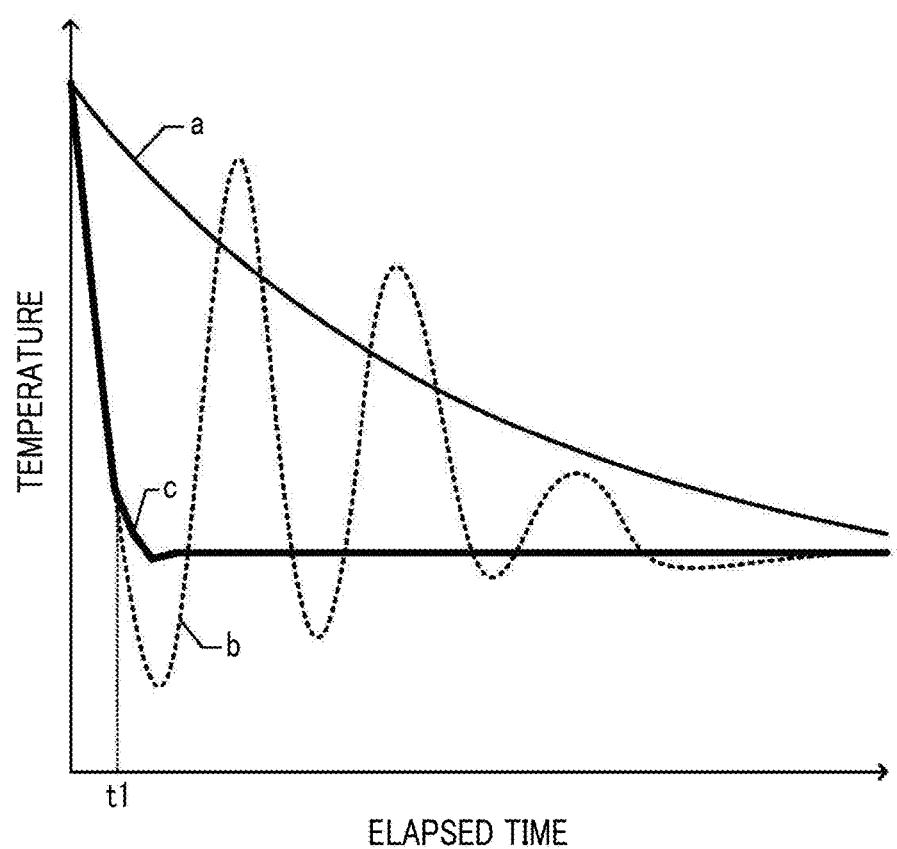
FIG. 3 is a graph illustrating an example of a simulation result of a rate of temperature change at a certain significant point of a simulation target.

Then, the FIRE will be described with reference to FIG. 3. FIG. 3 is a graph illustrating an example of a simulation result of a rate of temperature change at a certain significant point of a simulation target. A thin solid line a represents an example of a rate of temperature change obtained by numerically solving a normal heat conduction equation. In FIG. 3, an example in which temperature gradually decreases with the lapse of time is shown.

A broken line b in FIG. 3 represents an example of a rate of temperature change obtained by numerically solving the motion equation equivalent to the heat conduction equation in step 13 (FIG. 1). As described later, the attenuation coefficient of the motion equation does not almost affect the temperature field in the steady state. Accordingly, in a case where a temperature distribution in the steady state is to be calculated, the attenuation coefficient may be arbitrarily set.

In order to reduce the number of steps of numerical calculation until the temperature field enters the steady state, it is preferable that the attenuation coefficient is set to be small. If the attenuation coefficient is small, even if the same external force is applied, change in a calculation value of a temperature becomes large. Here, since the influence of an elastic term relatively becomes great, vibration occurs in the calculation value of the rate of temperature change.

If the motion equation equivalent to the heat conduction equation is solved by setting the attenuation coefficient to be small, as indicated by the broken line b, the change in the calculation result of the temperature obtained by the numerical calculation becomes steep. Further, the calculation value of the temperature comes close to the temperature in the steady state while being vibrated.

The calculation value of the temperature when the FIRE is applied is indicated by a solid line c. At a time point t1, it is assumed that the condition of step 16 (FIG. 1) is satisfied. At the time point t1, the rate of temperature change is set again to zero (step 17). Thus, the speed of the calculation value of the temperature at the time point t1 and thereafter becomes smooth once. As a result, the vibration of the calculation value of the temperature is reduced, and thus, a time until the temperature reaches the steady state becomes short.

An example of the condition of step 16 (FIG. 1) will be described. In each particle, a product of a first-order derivative of a temperature, a second-order derivative thereof, and a mass is calculated. A sum of products calculated with respect to all particles is calculated. As the condition of step 16, a condition that the sum is negative is employed. The fact that the product calculated for each particle is negative means that the direction of a rate of temperature change of each particle and the direction of an acceleration thereof are different from each other, that is, means that a temperature change is reduced. Accordingly, in a case where this condition is satisfied, it may be determined that the temperature field continues to come close to the steady state.

Figure 4:
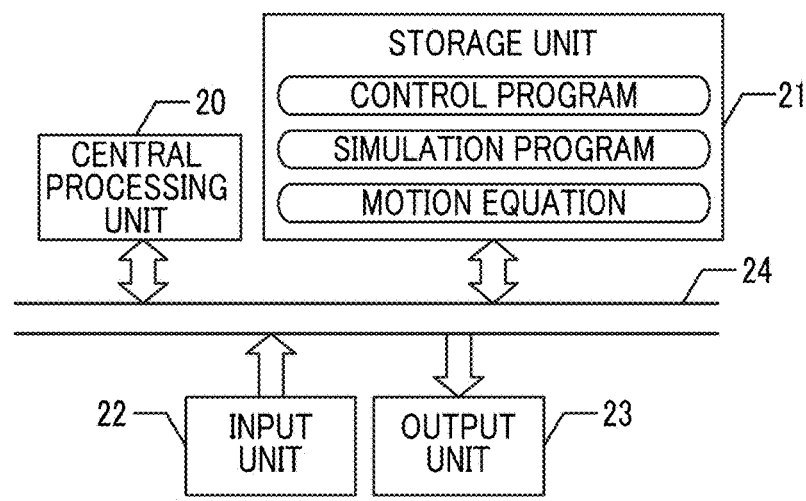
FIG. 4 is a block diagram illustrating a simulation apparatus that executes the simulation method according to the embodiment.

FIG. 4 is a block diagram illustrating a simulation apparatus (computer) that executes the simulation method according to the embodiment. A central processing unit 20, a storage unit 21, an input unit 22, and an output unit 23 are connected to each other through a data bus line 24.

Parameters which serve as a presumption condition for executing a simulation is input from the input unit 22. The parameters include an inter-particle potential, an external field, a density, a specific heat, a heat conduction coefficient, and the like, for example. The initial state of the particle determined in step 10 (FIG. 1) and the constraint condition thereof are also input through the input unit 22. As the input unit 22, a keyboard may be used, for example.

A control program, a simulation program, and various parameters that define a motion equation numerically calculated in a simulation, and the like are stored in the storage unit 21. The simulation program realizes a function for performing the simulation shown in FIG. 1. The central processing unit 20 executes the control program and the simulation program. If the simulation is terminated, the central processing unit 20 outputs a simulation result to the output unit 23. For example, the position of each particle may be displayed in a three-dimensional coordinate system, and the temperature of each particle may be displayed using color gradations.

Then, in step 13 (FIG. 1), the reason why the analysis of the temperature field can be performed by solving the heat conduction equation and the motion equation will be described.

A Lagrangian L of a classical scalar field $\phi$ may be expressed as the following expression as disclosed in Advanced Quantum Mechanics (Addison Wesley, 1967), for example.

[Expression 1]

$$L = \int \left[ \frac{1}{2} \{\rho(x)\dot{\phi}(x)^2 - \kappa(\nabla \phi(x))^2\} + Q(x)\phi(x) + \sum_x \lambda_s \delta^3(x-x_s)\sigma_s[\phi(x)] \right] d^3x \quad (1)$$

Here, $\sigma_s[\phi(x)]$ represents a constraint condition. $\lambda_s$ represents an undetermined constant of the Lagrangian. $\delta$ represents the $\delta$ Dirac function. An exponent 3 attached to $\delta$ and an exponent 3 attached to dx mean three-dimensions. $\Sigma$ means summing up with respect to x. When x is a value other than $x_s$, a value of the $\delta$ function is zero. In Expression (1), $\rho(x)$, $\kappa$, and $Q(x)$ do not mean specific physical quantities.

As the constraint condition $\sigma_s[\phi(x)]$, the Dirichlet boundary condition or the Neumman boundary condition may be used. The Dirichlet boundary condition may be expressed as the following expression.

[Expression 2]

$$\sigma_s[\phi(x)] = \phi_s - \phi_{s0} \quad (2)$$

Expression (2) means that $\phi(x)$ is a constant when $x = x_s$.

The Neumman boundary condition may be expressed as the following expression.

[Expression 3]

$$\sigma_s[\phi(x)] = \kappa \nabla_s \phi_s - q_s \quad (3)$$

Expression (3) means that a gradient of $\phi(x)$ is a constant when $x = x_s$. $\phi(x_s)$ is expressed as $\phi(s)$. $\nabla s$ represents a gradient at the position of $x = x_s$. $\phi_{s0}$ is a constant based on the constraint condition.

Expression (1) for defining the Lagrangian of a continuum is discretized on an one-dimensional superlattice, and a discretized scalar field is referred to as $\phi_i$. The Lagrangian L of the discretized scalar field $\phi_i$ is expressed as the following expression.

[Expression 4]

$$L = \sum_i \left[ \frac{1}{2} \{ \rho_i \dot{\phi}_i^2 - \kappa (\nabla_{i+1} \phi)^2 \} + Q_i \phi_i \right] \Delta V_i + \sum_x \lambda_s \sigma_s[\phi(x)] \quad (4)$$

Here, $\Delta V_i$ represents a linear volume element. $\nabla_{i \pm 1}$ represents a difference operator. The difference operator is defined as the following expression.

[Expression 5]

$$\nabla_{i+1} \phi = \frac{\phi_{i+1} - \phi_i}{\Delta} \quad (5)$$

Here, $\Delta$ represents an inter-particle distance.

If the scalar field $\phi_i$ is considered as particle attributes, for example, a speed, a temperature, and the like, $\phi_i$ satisfies the following Lagrange's motion equation.

[Expression 6]

$$\frac{d}{dt}\left( \frac{\partial L}{\partial \dot{\phi}_i} \right) - \frac{\partial L}{\partial \phi_i} = -\gamma_i \dot{\phi}_i \quad (6)$$

Here, $\gamma_i$ represents an attenuation coefficient. From Expression (4) and Expression (6), the following motion equation with respect to an i-th particle is obtained.

[Expression 7]

$$\rho_i \frac{d^2 \phi_i}{dt^2} = -\sum_{j=\pm 1} \frac{\kappa_{(i+j)/2}}{\Delta^2}(\phi_i - \phi_{i+j}) - \gamma_i \dot{\phi}_i + Q_i + \sum_s \frac{\lambda_s}{\Delta V_i} \frac{\partial \sigma_s[\phi(x)]}{\partial \phi_i} \quad (7)$$

Here, the first term on the right side in Expression (7) represents an elastic term, the second term thereof represents an attenuation term, the third term thereof represents an external force, and the fourth term thereof represents a constraint condition. $j = \pm 1$ below $\Sigma$ of the first term on the right side means that a sum with respect to particles on opposite sides of the i-th particle is used. s below $\Sigma$ of the fourth term on the right side corresponds to the number of constraint conditions.

In a steady state where $(d^2/dt^2)\phi_i$ becomes zero, Expression (7) may be transformed as follows.

[Expression 8]

$$\gamma_i \dot{\phi}_i = -\sum_{j=\pm 1} \frac{\kappa_{(i+j)/2}}{\Delta^2}(\phi_i - \phi_{i+j}) + Q_i + \sum_s \frac{\lambda_s}{\Delta V_i} \frac{\partial \sigma_s[\phi(x)]}{\partial \phi_i} \quad (8)$$

$$= \frac{\kappa_i}{\Delta^2}(\phi_{i+1} - 2\phi_i + \phi_{i-1}) + Q_i + \sum_s \frac{\lambda_s}{\Delta V_i} \frac{\partial \sigma_s[\phi(x)]}{\partial \phi_i}$$

Since the first term on the right side in Expression (8) represents difference approximation of $\kappa \nabla^2 \phi(x)$, Expression (8) results in a diffusion equation. Expression (8) is obtained under that assumption that the left side in Expression (7) is zero. Accordingly, if $\rho_i$ on the left side in Expression (7) is sufficiently small, it can be understood that a solution of Expression (6) comes close to a solution of the diffusion equation (8). That is, by solving Expression (6) using a numerical solution of an ordinary differential equation, it is possible to approximately solve the diffusion equation of Expression (8). As the numerical solution of the ordinary differential equation, the Verlet scheme, the Leap-frog scheme, the Gear method, or the like may be used.

The heat conduction equation may be expressed as the following expression.

[Expression 9]

$$\rho C_v \frac{\partial T}{\partial t} = \nabla \cdot [K \nabla T] + Q \quad (9)$$

Here, $\rho$ represents density, $C_v$ represents specific heat, T represents temperature, t represents time, K represents heat conductivity, and Q represents a calorific value per unit volume.

If $\phi_i$, $\gamma_i$, $\kappa_i$, and $Q_i$ in Expression (8) are respectively considered as the temperature T, a product of the density $\rho$ and the specific heat Cv, the heat conductivity K, and the calorific value Q, it can be understood that Expression (8) is the same form as that of the heat conduction equation of Expression (9). Specifically, a term of a spatial distribution of $\phi_i$ in Expression (8) and a term of a derivative of $\phi_i$ with respect to time may be associated with a term of a spatial temperature distribution and a term of a derivative of temperature with respect to time in Expression (9), respectively. Thus, under the condition that $\rho_i$ is sufficiently small, it can be said that the motion equation of Expression (7) is equivalent to the heat conduction equation of Expression (9).

Hereinbefore, a case where the classical scalar field $\phi$ is discretized on the one-dimensional superlattice has been described. In order to expand the above-mentioned theory to a three-dimensional complicated shape, a finite volume method may be applied to Expression (7). If the finite volume method is applied to Expression (7), the following expression is obtained.

[Expression 10]

$$m_i \frac{d^2\phi_i}{dt^2} = -\sum_{j=nm} \frac{\kappa_{(i+j)/2}}{r_{ij}}(\phi_i - \phi_j)\Delta S_{ij} + (Q_i - \gamma_i \dot\phi_i)\Delta V_i + \sum_s \lambda_s \frac{\partial \sigma_s[\phi]}{\partial \phi_i} \quad (10)$$

Here, Σ of the first term on the right side in Expression (10) means that summing-up is performed with respect to all particles which are in contact with an i-th particle. $\Delta S_{ij}$ represents an area of a contact surface between the Voronoi polyhedrons i and j. $m_i$ is expressed as the following expression.

[Expression 11]

$$m_i = \rho_i \Delta V_i \quad (11)$$

$m_i$ is a parameter corresponding to a mass in the motion equation, and thus, $m_i$ is referred to as a virtual mass.

The virtual mass $m_i$ should satisfy the following lower limit condition from a stability condition of numerical integration.

[Expression 12]

$$m_i > \frac{\gamma_i \Delta V_i dt}{2} \cap m_i \geq \kappa_{(i+j)/2} \frac{\Delta S_{ij}}{r_{ij}} \left(\frac{dt}{2\pi}\right)^2, \forall j \quad (12)$$

With respect to a time pitch dt, an optimal value may be determined based on an inter-particle distance (mesh size) and a sound speed when the structural-elastic phenomenon is analyzed. The lower limit value of the virtual mass $m_i$ is determined from the time pitch dt determined based on the structural-elastic phenomenon and Expression (12). Further, as described above, under the condition that $\rho_i$ is sufficiently small, the solution of Expression (6) comes close to the solution of the diffusion equation (8). Thus, it is preferable that $\rho_i$ is sufficiently smaller than a true density ρ of a simulation target. That is, it is preferable that the following expression is satisfied.

[Expression 13]

$$\rho \Delta V_i >> m_i \quad (13)$$

By replacing $\gamma_i$ in Expression (10) with a product of a density $\rho_i$ and a specific heat $C_{vi}$ and replacing $\phi_i$ with a temperature $T_i$, the following expression is obtained. $C_{vi}$ represents a specific heat at the position of the i-th particle.

[Expression 14]

$$\gamma_i \to \rho_i C_{vi}$$
$$\phi_i \to T_i$$
$$m_i \frac{d^2 T_i}{dt^2} =$$
$$-\sum_{j=nm} \frac{\kappa_{(i+j)/2}}{r_{ij}}(T_i - T_j)\Delta S_{ij} + (Q_i - \rho_i C_{vi} \dot T_i)\Delta V_i + \sum_s \lambda_s \frac{\partial \sigma_s[\phi]}{\partial \phi_i} \quad (14)$$

By solving Expression (14) which is the same form as that of the motion equation, it is possible to perform a simulation of a temperature field. Since $\phi_i$ in Expression (10) is replaced with $T_i$ in Expression (14), the dimension of $m_i$ in Expression (14) is different from the dimension of $m_i$ in Expressions (10) and (11). It can be understood that the dimension of the virtual mass $m_i$ is the same as the dimension of the product of the density $\rho_i$, the specific heat $C_v$, the volume element $\Delta V_i$, and the time pitch dt from a term including $\Delta V_i$ on the right side in Expression (14). That is, the dimension of the virtual mass $m_i$ becomes [J/K] [s].

From Expression (12), a satisfactory condition of the virtual mass $m_i$ is given as the following expression.

[Expression 15]

$$m_i > \frac{\rho_i C_{vi} \Delta V_i dt}{2} \cap m_i \geq \kappa_{(i+j)/2} \frac{\Delta S_{ij}}{r_{ij}} \left(\frac{dt}{2\pi}\right)^2, \forall j \quad (15)$$

Furthermore, a satisfactory condition of the virtual mass $m_i$ is empirically given as the following expression from a result of various numerical calculations.

[Expression 16]

$$\rho_i C_{vi} \Delta V_i \tau >> m_i$$
$$10 dt < \tau < 100 dt \quad (16)$$

From Expression (15) and Expression (16), it is recommended that $m_i$ be set as expressed in the following expression, as an example.

[Expression 17]

$$m_i = 10 \rho C_v \Delta V_i dt \quad (17)$$

As described above, by solving the motion equation (14) equivalent to the heat conduction equation (9), it is possible to perform analysis of a temperature field.

In step 13 (FIG. 1), if the attenuation coefficient $\gamma_i$ in the motion equation (7) is set to zero, and $\rho_i C_{vi}$ in Expression (14) are set to zero, a calculation result of the speed of the temperature T becomes large. That is, a temporal change of the temperature T becomes steep. Thus, it is possible to reduce the time until the calculation value of the temperature reaches the temperature in the steady state.

Then, in step 132 (FIG. 2), even if the attenuation coefficient $\gamma_i$ or $\rho_i C_{vi}$ is set to a value different from an original value or zero, it is possible to calculate an accurate temperature in a steady state.

Figure 5:
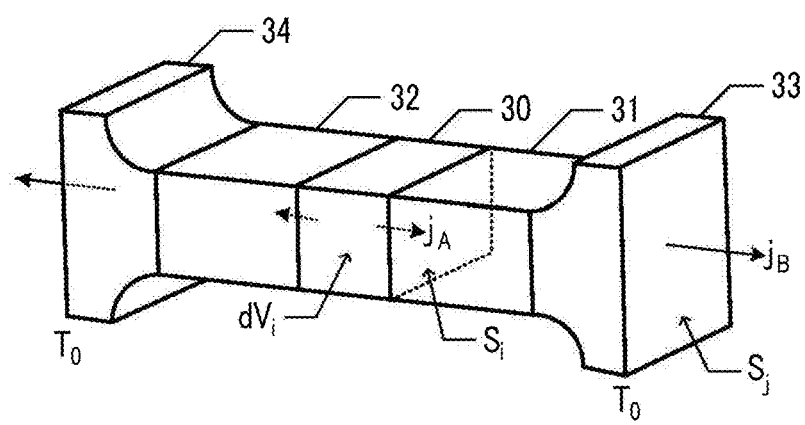
FIG. 5 is a perspective view illustrating a model for showing that it is possible to calculate an accurate temperature in a steady state even when an attenuation coefficient of a motion equation equivalent to a heat conduction equation is set as a value different from an original value.

A rod-shaped model shown in FIG. 5 will be described. A heat source having a calorific value $Q_i$ per unit volume is present in a central region 30 of a volume $dV_i$. Heat conduction occurs toward intermediate regions 31 and 32 on opposite sides through interfaces of an area $S_i$ from the central region 30. End portion regions 33 and 34 are connected to ends of the intermediate regions 31 and 32, respectively. The end portion regions 33 and 34 are in contact with a hot bath at a temperature $T_0$ on end surfaces of an area $S_j$, respectively.

Heat energy $j_A$ per unit area and per unit time flowing from the central region 30 to one intermediate region 31 is expressed as the following expression.

[Expression 18]

$$j_A = \frac{Q_i dV_i}{2 S_i} \quad (18)$$

When a temperature of the end portion region 33 is represented as T and a heat transfer coefficient between the end portion region 33 and the hot bath is represented as h, heat energy $j_B$ per unit area and per unit time flowing from the end portion region 33 to the hot bath is expressed as the following expression.

[Expression 19]

$$j_B = h(T - T_0) \quad (19)$$

The heat energy per unit time flowing from the central region 30 to the intermediate region 31 is the same as the heat energy per unit time flowing from the end portion region 33 to the hot bath. Thus, the following expression is established.

[Expression 20]

$$j_A S_i = j_B S_j \quad (20)$$

The following expression is derived from Expression (18) to Expression (20).

[Expression 21]

$$T - T_0 = \frac{Q_i dV_i}{2hS_j} \quad (21)$$

From Expression (21), it can be understood that a surface temperature in a steady state is determined only a calorific value from a heat source and a surface area of a simulation target. The surface temperature in the steady state does not depend on a density and a specific heat. Accordingly, even if the motion equation (14) is solved in a case where the attenuation coefficient $\rho_i C_{vi}$ in Expression (14) is set to an arbitrary value or zero, it is possible to calculate the surface temperature in the steady state.

If the attenuation coefficient $\rho_i C_{vi}$ is set to be small, as indicated by the broken line b in FIG. 3, vibration occurs in calculation values of temperatures. The vibration is attenuated according to the size of the attenuation coefficient $\rho_i C_{vi}$, and the calculation values of the temperatures are converged on the temperature in the steady state.

If the attenuation coefficient $\rho_i C_{vi}$ is set to be zero, the vibration is not attenuated and is continuously present. In this embodiment, the vibration of the calculation values of the temperatures is converged in a short time by applying FIRE thereto, as indicated by the solid line c in FIG. 3.

During a period of time until a temperature field reaches a steady state, that is, a period of time when an attenuation coefficient is set to a value different from an original value to execute step 13, a substantial meaning of a time pitch when solving a motion equation equivalent to a heat conduction equation is different from the time pitch applied to dynamic analysis in step 11 (FIG. 1). Thus, a time development of a structural-elastic phenomenon of a simulation target and a time development of a heat conduction phenomenon are performed in a non-synchronous manner. If the original value is set as the attenuation coefficient after the temperature field reaches the steady state, the time development of the structural-elastic phenomenon of the simulation target and the time development of the heat conduction phenomenon are synchronized.

In order to check effects of the simulation method according to this embodiment, a simulation of a temperature field of an object was performed. Hereinafter, the simulation result will be described with reference to FIGS. 6A, 6B, and FIG. 7.

Figure 6A:
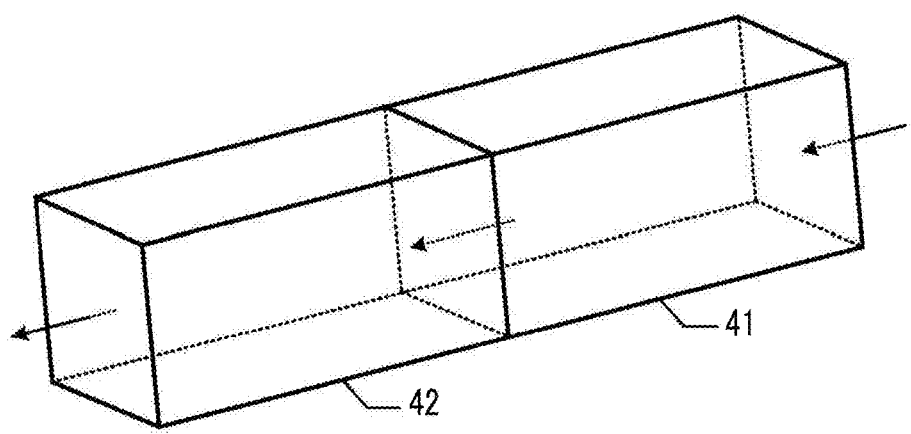
FIG. 6A is a perspective view illustrating a simulation target.

FIG. 6A is a perspective view illustrating a simulation target. An end surface on a left side of a quadrangular prism-shaped object 41 and an end surface on a right side of a quadrangular prism-shaped object 42 are thermally in contact with each other. Lengths of the object 41 and the object 42 are 20 mm. Further, cross-sections thereof orthogonal to a length direction are squares, and areas thereof are equal to each other.

Heat energy flows from the right end of the object 41 to the object 41. Heat is transferred from the object 41 to the object 42 through a contact surface between the right end of the object 41 and the left end of the object 42. Heat energy flows out from the left end of the object 42. Heat energy per unit time flowing into the object 41 and heat energy per unit time flowing out from the left end of the object 42 are equal to each other. Thus, heat balance between the object 41 and the object 42 is maintained as zero. A temperature field of the objects 41 and 42 finally reaches a steady state. That is, the rate of temperature change becomes zero.

Figure 6B:
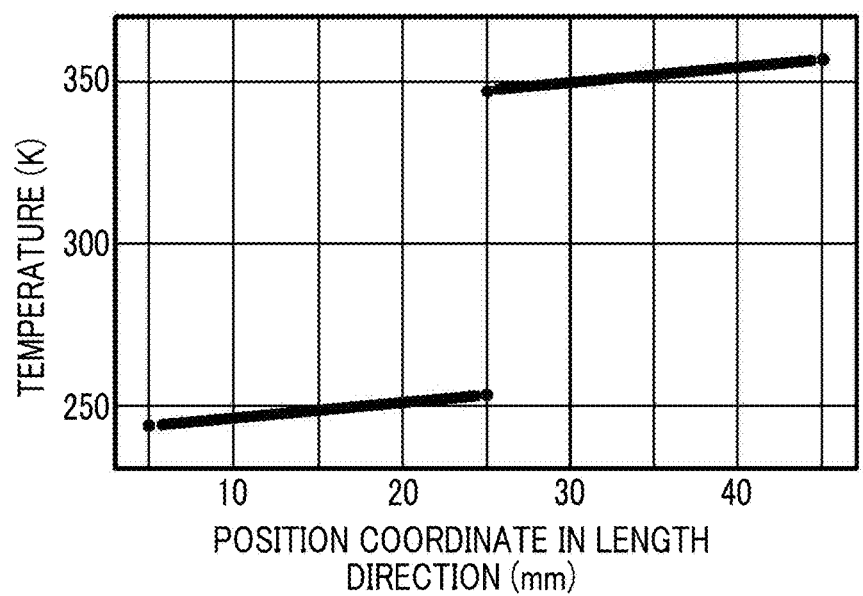
FIG. 6B is a graph illustrating a simulation result of a temperature distribution in a length direction of a simulation target when the simulation target reaches a steady state.

FIG. 6B illustrates a simulation result of a temperature distribution in a length direction of the objects 41 and 42 when the temperature field reaches the steady state. A position coordinate of the left end of the object 42 is 5 mm, a position coordinate of the contact surface between the objects 41 and 42 is 25 mm, and a position coordinate of the right end of the object 41 is 45 mm. Since heat energy flows into the object 41 from the position of the coordinate 45 mm and heat energy flows out from the position of the coordinate 5 mm, a temperature gradient becomes negative. Discontinuity of temperature based on a heat transfer coefficient of the contact surface between the objects 41 and 42 occurs at the position of the coordinate 25 mm.

Figure 7:
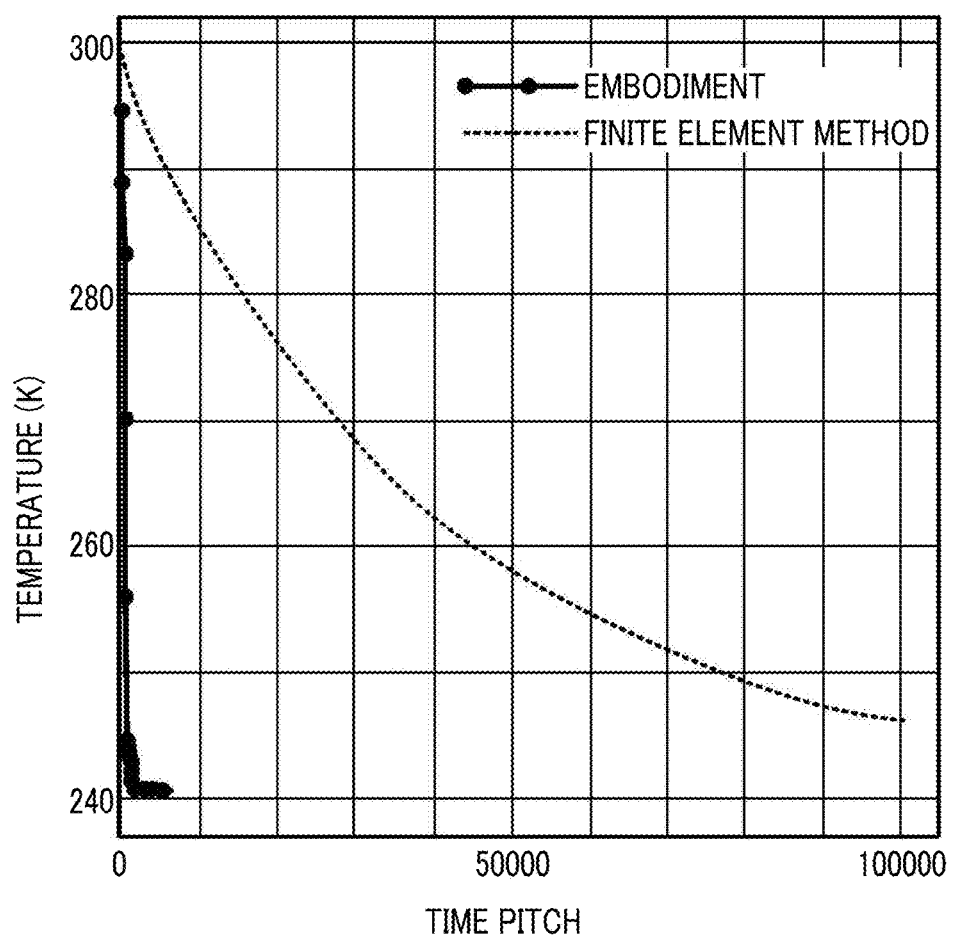
FIG. 7 is a graph illustrating a simulation result of a rate of temperature change of one particle positioned at a left end of the simulation target (FIG. 6A).

FIG. 7 illustrates a simulation result of a rate of temperature change of one particle disposed at the left end of the object 42 (FIG. 6A). A transverse axis represents a time pitch of a simulation, and a longitudinal axis represents a temperature as a unit "K". A broken line in FIG. 7 represents a result obtained by performing a simulation using a general finite element method, and a solid line represents a result obtained by performing a simulation using the method according to this embodiment. A black circle mark attached on the solid line represents a simulation result of a temperature at a time point when one time pitch is terminated.

It can be understood that during a period of time taken until a temperature of the left end of the object 42 reaches a temperature of the steady state, a rate of temperature change calculated by the simulation according to this embodiment is larger than a rate of temperature change calculated using the finite element method. Thus, it is possible to cause the heat conduction phenomenon to reach the steady state with a small number of time pitches. This is an effect obtained by setting the attenuation coefficient of the motion equation equivalent to the heat conduction equation in step 132 (FIG. 2) to zero.

If the attenuation coefficient of the motion equation is set to zero, a vibration waveform normally appears in a simulation result. However, a vibration waveform does not appear in the simulation result illustrated in FIG. 7. This is an effect obtained by executing a process (FIRE) of setting the rate of temperature change of each particle to zero in step 17 (FIG. 1) in a case where the heat conduction phenomenon does not reach the steady state and it is determined that the condition is satisfied in step 16 (FIG. 1).

In the example illustrated in FIG. 7, in a region where a calculation value of a temperature is equal to or greater than 250 K, it is determined in step 16 (FIG. 1) that the condition is not satisfied. Thus, the calculation value of the temperature rapidly decreases. In an initial time pitch where the calculation value of the temperature is equal to or smaller than 250 K, it is determined in step 16 (FIG. 1) that the condition is satisfied. Thus, a measurement degree of the decrease of the calculation value of the temperature rapidly becomes small.

If the calculation value of the temperature reaches about 240 K, it is determined in step 131 (FIG. 2) that the heat conduction phenomenon reaches the steady state. Thus, an original value is set as the attenuation coefficient of the motion equation equivalent to the heat conduction equation (step 133 in FIG. 2). Thus, an original temperature change of the particle at the left end of the object 42 is reflected in the change in the calculation value of the temperature.

As illustrated in FIG. 7, by using the simulation method according to this embodiment, it is possible to reduce the number of time pitches until the temperature field reaches the steady state. When a simulation was actually performed using the method according to this embodiment, it could be understood that the steady state of the temperature field was obtained at a high speed 20 times or faster compared with a case where the finite element method in the related art was used.

A preferable time pitch when a temperature field is simulated is about 10000 times a preferable time pitch when a structural-elastic phenomenon is simulated. Accordingly, in a method of executing analysis of the temperature field and analysis of the structural-elastic phenomenon in combination with the same time pitch, the number of time pitches in numerical calculation until the temperature field reaches the steady state becomes massive. Thus, in reality, it is not possible to perform a simulation until the temperature field reaches to the steady state.

In the above-described embodiment, since it is possible to arbitrarily set the attenuation coefficient of the motion equation equivalent to the heat conduction equation, it is possible to make a time constant of the temperature change close to a time constant of the structural-elastic phenomenon. Thus, by coupling the analysis of the heat conduction phenomenon and the analysis of the structural-elastic phenomenon, it is possible to perform the simulation until the heat conduction phenomenon reaches the steady state.

Then, before describing another embodiment, a simulation method based on a reference example will be described with reference to FIG. 8 to FIG. 10B. Hereinafter, a point different from the embodiment described with reference to FIGS. 1 to 7 will be described, and description about common configurations will not be repeated.

Figure 8:
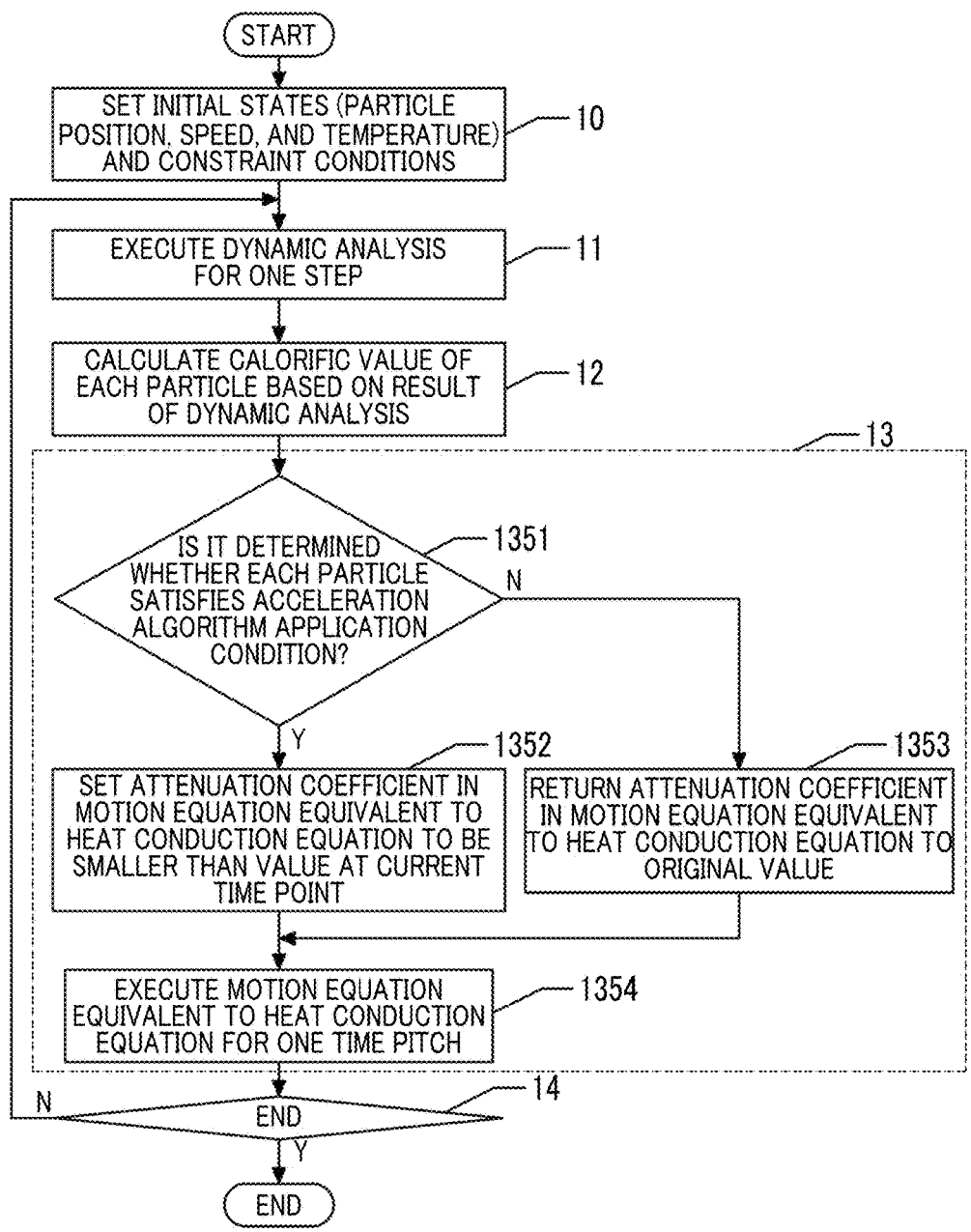
FIG. 8 is a flowchart illustrating a simulation method according to a reference example.

FIG. 8 is a flowchart illustrating the simulation method according to the reference example. Steps 10 to 12 of the simulation method according to this reference example are the same as steps 10 to 12 of the embodiment illustrated in FIG. 1. Step 13 of the simulation method according to this reference example is different from step 13 of the embodiment illustrated in FIG. 1. Hereinafter, a process of step 13 will be described.

First, it is determined in step 1351 whether each particle in a temperature field satisfies an acceleration algorithm application condition, for each particle.

Hereinafter, the acceleration algorithm application condition will be described. A determination parameter $P_i$ is defined as follows.

[Expression 22]

$$P_i = F_i v_i \quad (22)$$
$$F_i = m_i \frac{d^2 T_i}{dt^2}$$
$$v_i = \frac{dT_i}{dt}$$

$F_i$ is a product of a second-order derivative of a temperature $T_i$ of an article i and a virtual mass $m_i$. This $F_i$ corresponds to a force for changing a temperature of the particle i. When $F_i$ is positive, it is considered that a force in a direction where a temperature increases acts on the particle i, and when $F_i$ is negative, it is considered that a force in a direction where the temperature decreases acts on the particle i. The sign of $F_i$ is the same as the sign of an acceleration of change in the temperature $T_i$. $V_i$ corresponds to a rate of temperature change of the particle i.

When the determination parameter $P_i$ is positive, the acceleration algorithm application condition is satisfied, and when the determination parameter $P_i$ is negative or zero, it is determined that the acceleration algorithm application condition is not satisfied.

Then, a physical meaning of the determination parameter $P_i$ will be described. The fact that the determination parameter $P_i$ is positive means that the sign of the acceleration of change in the temperature $T_i$ and the sign of the rate of change in the temperature $T_i$ are the same. That is, in a case where the determination parameter $P_i$ is positive, when the temperature $T_i$ increases, a force for further increasing a rising rate of the temperature $T_i$ acts on the particle i. Contrarily, when the temperature $T_i$ decreases, a force for further increasing a lowering rate of the temperature Ti acts on the particle i. This state may be considered as a state where the temperature $T_i$ does not reach the steady state and is changing toward the steady state.

The fact that the determination parameter $P_i$ is negative means that a force for decreasing the rising rate of the temperature $T_i$ or a force for decreasing the lowering rate of the temperature $T_i$ acts on the particle i. Accordingly, when the determination parameter $P_i$ is negative, it is considered that the temperature $T_i$ of the particle i is close to the steady state.

When the determination parameter $P_i$ is positive, it is determined that the acceleration algorithm application condition is satisfied, and when the determination parameter $P_i$ is negative, it is determined that the acceleration algorithm application condition is not satisfied. In a case where the determination parameter $P_i$ is zero, it may be determined that the acceleration algorithm application condition is satisfied or is not satisfied. In this embodiment, when the determination parameter $P_i$ is zero, it is determined that the acceleration algorithm application condition is not satisfied.

In a case where it is determined in step 1351 that the acceleration algorithm application condition is satisfied, that is, in a case where the sign of the rate of change in the temperature $T_i$ and the sign of the acceleration of change in the temperature $T_i$ are the same, in step 1352, the attenuation coefficient of the motion equation equivalent to the heat conduction equation is set to be smaller than a value at a current time point.

Specifically, $\rho_i C_{vi} \Delta V_i$ which is the attenuation coefficient (coefficient of Ti dot) of the motion equation (Expression 14) equivalent to the heat conduction equation is set to be smaller than a value at a current time point. For example, the attenuation coefficient is set to be 0.5 times a value at a current time point. By setting the attenuation coefficient to be small, it is possible to make the temperature change steeper.

In a case where it is determined in step 1351 that the acceleration algorithm application condition is not satisfied, that is, in a case where the sign of the rate of change in the temperature $T_i$ and the sign of the acceleration of change in the temperature $T_i$ are different from each other, in step 1353, $\rho_i C_{vi} \Delta V_i$ which is the attenuation coefficient (coefficient of Ti dot) of the motion equation (Expression 14) equivalent to the heat conduction equation is restored to an original value.

After steps 1352 and 1353, in step 1354, the motion equation (Expression 14) is executed for one time pitch using the attenuation coefficient after correction. Then, in step 14, it is determined whether a simulation termination condition is satisfied. The determination condition may be set to be the same as that in step 14 illustrated in FIG. 1. In a case where the simulation termination condition is satisfied, the simulation is terminated. In a case where the simulation termination condition is not satisfied, the procedure returns to step 11 to continue the simulation.

Then, a result obtained by actually performing a simulation using the simulation method illustrated in FIG. 8 will be described. A simulation of a temperature change when a simple bearing was operated was performed.

Figure 9:
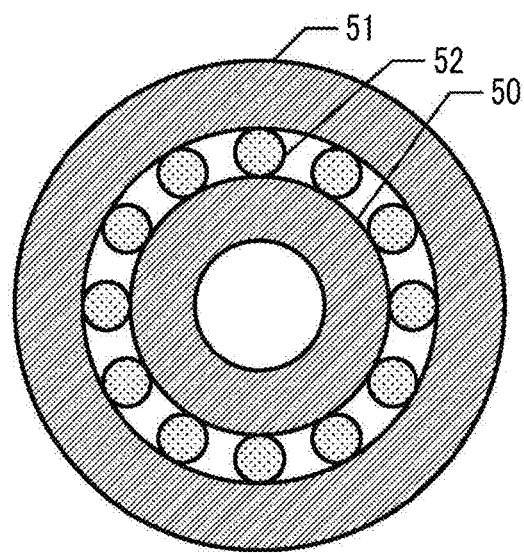
FIG. 9 is a sectional view illustrating a simple bearing which is a simulation target.

FIG. 9 is a sectional view illustrating a simple bearing which is a simulation target. The bearing which is the simulation target is configured by an inner ring 50, an outer ring 51, and twelve rollers 52 which are arranged between the inner ring 50 and the outer ring 51. An outer peripheral surface of the outer ring 51 was in contact with outside air of a temperature of 300 K, and the inner ring 50 was forcibly rotated at a rotation speed of 3600 rpm. A heat transfer rate on an interface between the outer peripheral surface of the outer ring 51 and the outside air was set to be 5,000 W/m$^2$/K. As heat transfer rates of the inner ring 50, the outer ring 51, and the rollers 52, a value of a general stainless steel was used.

When a contact force of a particle i and a particle j is represented as $f_{ij}$, a relative speed of the particle i and the particle j is represented as $v_{ij}$, and a frictional coefficient between the particle i and the particle j is represented as $\mu_{ij}$, a calorific value $Q_i$ per unit volume of the particle i is expressed as the following expression.

[Expression 23]

$$Q_i = \sum_{j \neq i} |\mu_{ij} f_{ij} v_{ij}| \qquad (23)$$

FIG. 10A is a graph illustrating change in the overall temperature calculated using the simulation method according to the reference example in FIG. 9. A transverse axis represents an elapsed time as a unit "s", and a longitudinal axis represents a temperature as a unit "K". For comparison, a result obtained by performing a simulation by fixing an attenuation coefficient to an original value is shown in FIG. 10B. Here, the "overall temperature" means an average value of temperatures of all particles that form a temperature field.

When comparing FIG. 10A with FIG. 10B, it can be understood that a time until a temperature field reaches a steady state is remarkably short in the simulation result in FIG. 10A. This is an effect obtained by setting the attenuation coefficient to be small in step 1352 in FIG. 8. In the simulation result of FIG. 10B, the overall temperature is converged to 319 K, but in the simulation result of FIG. 10A, it can be understood that the overall temperature vibrates in a range of about width 1.0 K even after the temperature field reaches the steady state.

Hereinafter, a cause of the vibration of the overall temperature vibrates even after the temperature field reaches the steady state will be described. In the simulation target illustrated in FIG. 6A, flowing-in and flowing-out of heat energy were uniformly maintained with the lapse of time. On the other hand, in the simulation target illustrated in FIG. 9, a heating place and a calorific value are changed with the lapse of time. Thus, even after the temperature field reaches the steady state, heat flowing is temporally and spatially changed in the simulation target. As a result, in view of individual particles, even after the acceleration algorithm application condition in step 1351 (FIG. 8) is not satisfied (even after it is considered that the temperature field reaches the steady state), there is a case where the acceleration algorithm application condition is satisfied again. In this way, since a state where the acceleration algorithm application condition is satisfied and a case where acceleration algorithm application condition is not satisfied are repeated, it is considered that the overall temperature vibrates.

Next, an embodiment capable of removing vibration of the overall temperature will be described with reference to FIG. 11 and FIG. 12.

FIG. 11 is a flowchart illustrating a simulation method according to this embodiment. Hereinafter, a point different from the flowchart illustrated in FIG. 8 will be described, and description about common processes will not be repeated.

In the embodiment illustrated in FIG. 11, in step 136 before step 1351, it is determined whether the attenuation coefficient is to be fixed. In a case where it is determined that the attenuation coefficient is to be fixed, in step 1353, the attenuation coefficient is restored to an original value. That is, step 1352 of setting the attenuation coefficient to be smaller than a value of at a current time point is not executed. If the attenuation coefficient is once fixed, thereafter, the attenuation coefficient maintains the fixed state.

As a determination condition relating to whether the attenuation coefficient is to be fixed, an elapsed time from the start of a simulation or the number of time pitches may be used. In this case, if the elapsed time or the number of time pitches exceeds a determination upper limit value, the attenuation coefficient may be fixed to an original value. At a time point determined that the temperature field reaches the steady state, the attenuation coefficient may be fixed to the original value.

Figure 12:
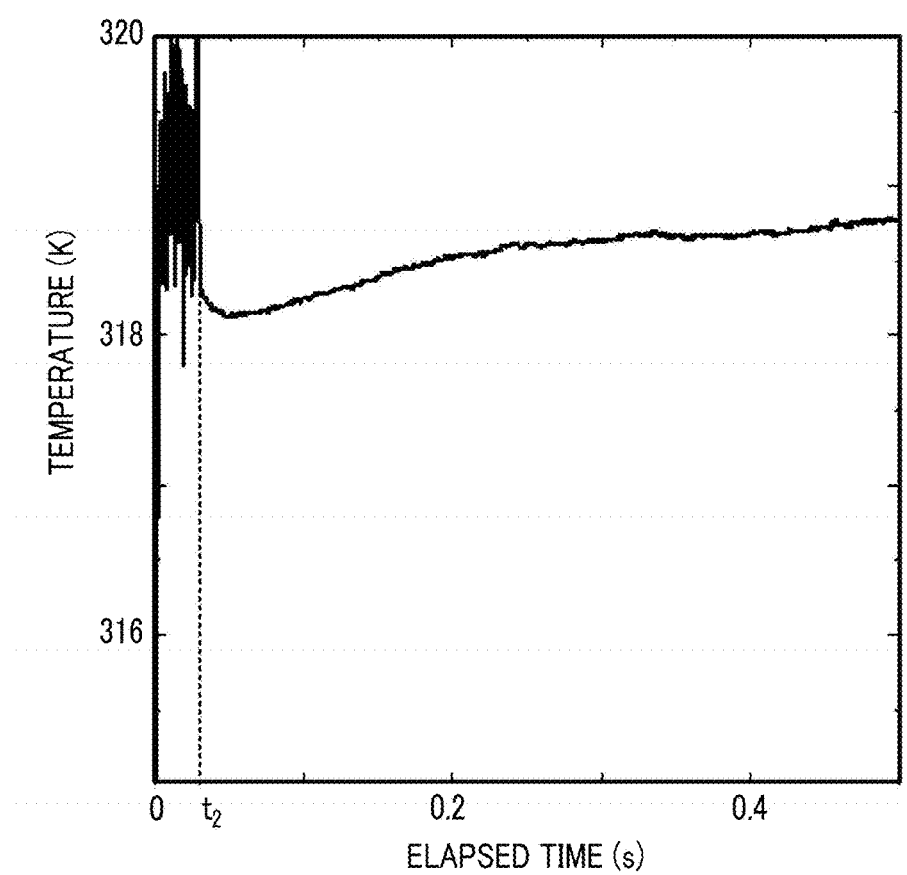
FIG. 12 is a graph illustrating a result of a temperature change of the bearing shown in FIG. 9 obtained using the simulation method according to the embodiment shown in FIG. 11.

FIG. 12 illustrates a result of a temperature change of the bearing shown in FIG. 9 obtained using the simulation method according to the embodiment shown in FIG. 11. A transverse axis represents an elapsed time as a unit "s", and a longitudinal axis represents a temperature as a unit "K". At a time point t2, an attenuation coefficient is fixed. It can be understood that until the attenuation coefficient is fixed, the overall temperature vibrates, but after the attenuation coefficient is fixed at the time point t2, the vibration does not occur.

Since the simulation is performed in a similar way to the reference example shown in FIG. 8 until the attenuation coefficient is fixed, it is possible to reduce a simulation time until the temperature field reaches the steady state. Further, in this embodiment, after the attenuation coefficient is fixed, it is possible to prevent vibration of the overall temperature.

Next, still another embodiment will be described with reference to FIGS. 13 and 14. Hereinafter, a point different from the reference example described with reference to FIG. 8 will be described, and description about common processes will not be repeated.

Figure 13:
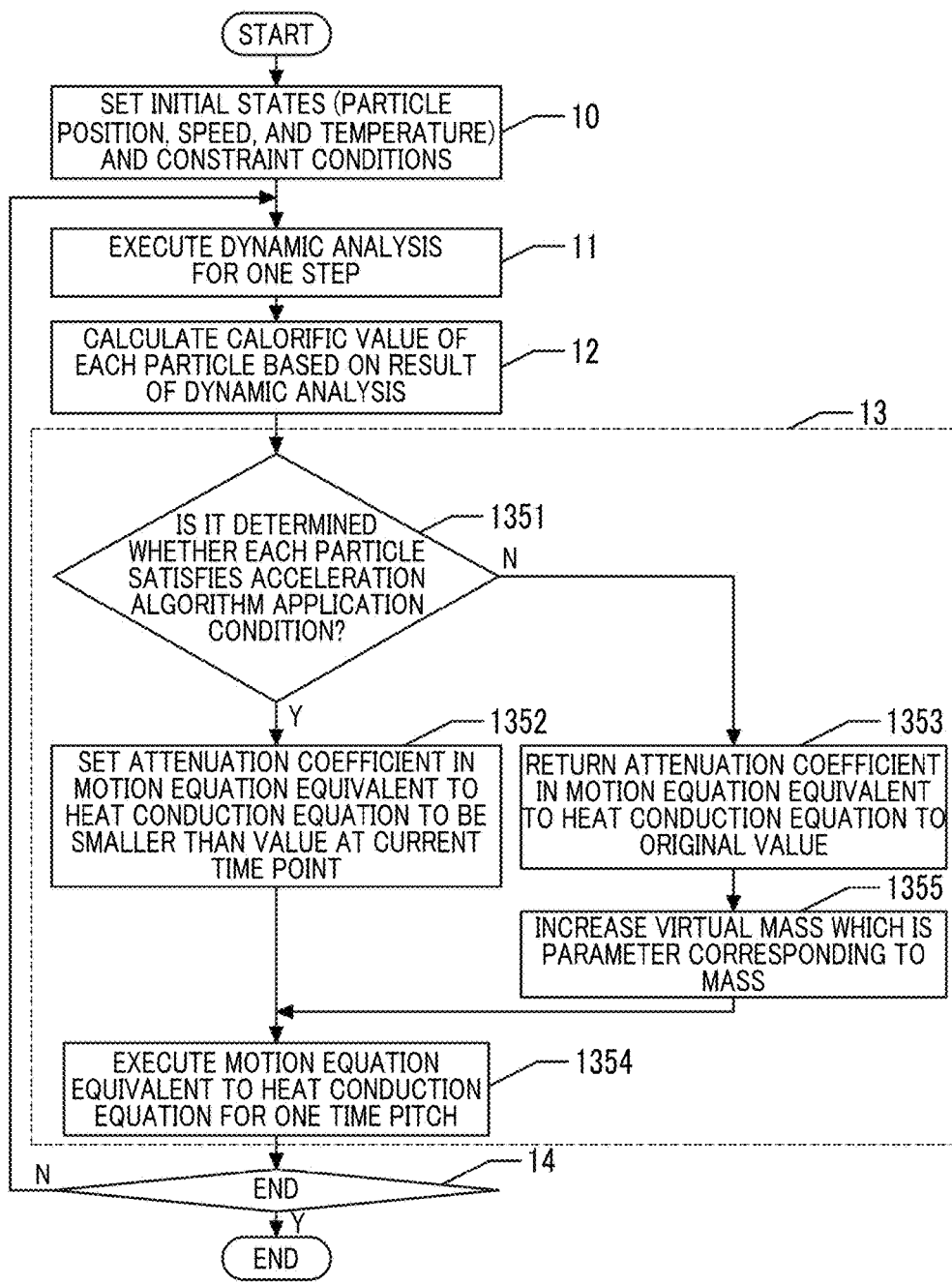
FIG. 13 is a flowchart illustrating a simulation method according to still another embodiment.

FIG. 13 is a flowchart illustrating a simulation method according to this embodiment. In this embodiment, after step 1353 is executed, or before step 1353 is executed, step 1355 is further executed. In step 1355, a virtual mass $m_i$ which is a parameter corresponding to a mass in a motion equation equivalent to a thermal motion equation is increased to become greater than a virtual mass $m_i$ at a current time point.

If it is determined in step 1351 that the acceleration algorithm application condition is satisfied, even after the attenuation coefficient is restored to the original value in step 1353, the attenuation coefficient becomes smaller than the original value again. On the other hand, if the virtual mass $m_i$ is once increased, even in a case where it is determined that the acceleration algorithm application condition is satisfied in step 1351, the virtual mass $m_i$ does not return to the original value. That is, the virtual mass $m_i$ maintains the increased state.

Hereinafter, the process of step 1355 will be described in detail. In step 1355, the virtual mass $m_i$ is set to be 1.05 times a value at a current time point, for example. Here, in a case where the virtual mass $m_i$ after increase exceeds a predetermined upper limit value $m_{imax}$, the virtual mass $m_i$ is set to be equal to the upper limit value $m_{imax}$. Accordingly, there is no case where the virtual mass $m_i$ exceeds the upper limit value $m_{imax}$.

Figure 14:
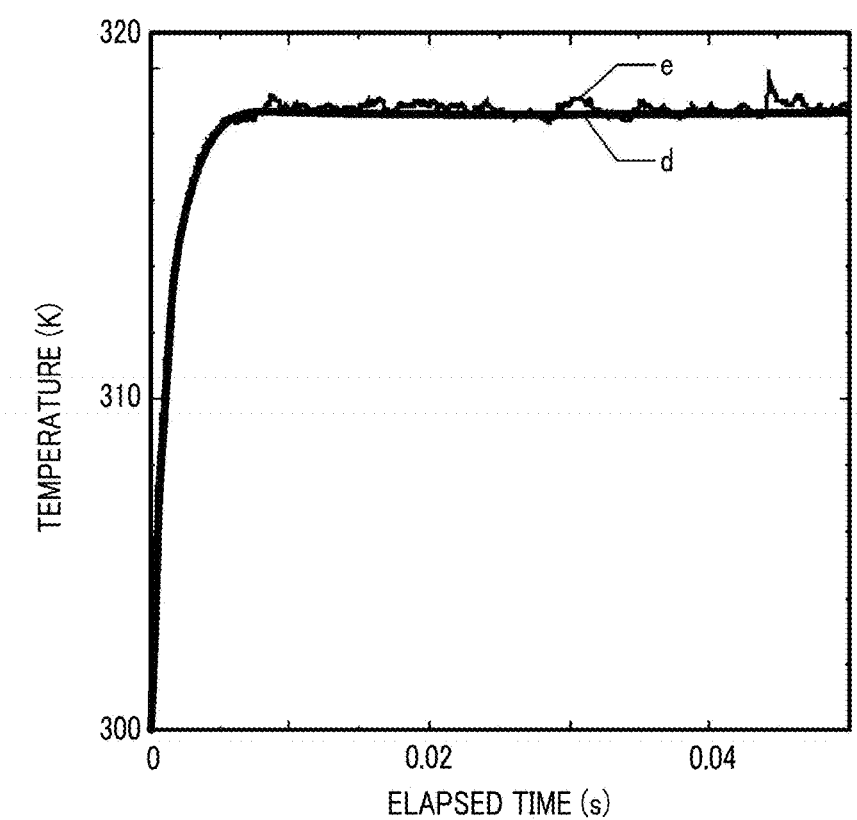
FIG. 14 is a graph illustrating a result of a temperature change of the bearing shown in FIG. 9 obtained using the simulation method according to the embodiment shown in FIG. 13.

FIG. 14 illustrates a result of a temperature change of the bearing shown in FIG. 9 obtained using the simulation method according to the embodiment shown in FIG. 13. A transverse axis represents an elapsed time as a unit "s", and a longitudinal axis represents a temperature as a unit "K". A thick solid-line d in FIG. 14 represents a calculation result of the overall temperature in a case where the simulation method according to the embodiment illustrated in FIG. 13 is used, and a thin solid-line e represents a calculation result of the overall temperature in a case where the simulation method according to the reference example illustrated in FIG. 8 is used.

Times until a temperature field reaches a steady state are approximately the same in the reference example illustrated in FIG. 8 and the embodiment illustrated in FIG. 13. It can be understood that in the case of the reference example illustrated in FIG. 8, vibration remains in the overall temperature after the temperature field reaches the steady state, but in the case of the embodiment illustrated in FIG. 13, the vibration is suppressed.

In the embodiment illustrated in FIG. 13, after the temperature field reaches the steady state, the virtual mass $m_i$ increases, and the increased virtual mass $m_i$ is not reduced. If the virtual mass $m_i$ increases, a temperature change of each particle i becomes smooth. As a result, the vibration of the overall temperature after the temperature field reaches the steady state is prevented. Further, until the temperature field reaches the steady state, a frequency that the acceleration algorithm application condition is satisfied in step 1351 (FIG. 13) is low. Accordingly, it is possible to prevent the virtual mass $m_i$ from greatly increasing before the temperature field reaches the steady state. Thus, until the temperature field reaches the steady state, a steep temperature change is obtained.

Since the virtual mass $m_i$ and the attenuation coefficient return to the original values after the overall temperature is converged on a constant value without vibration, the same termination state as in FIG. 10B is obtained.

Hereinbefore, the present invention has been described with reference to the embodiments, but the present invention is not limited thereto. It is obvious to those skilled in the art that various modifications, replacements, combinations and the like may be made, for example.

It should be understood that the invention is not limited to the above-described embodiment, but may be modified into various forms on the basis of the spirit of the invention. Additionally, the modifications are included in the scope of the invention.

What is claimed is:

1. A computer program product embodied on a tangible, non-transitory computer-readable data storage device, the computer program product causes a computer to execute a coupled simulation of a structural-elastic phenomenon and a heat conduction phenomenon of a simulation target including a plurality of particles, the computer program product comprising:

computer code for performing numerical calculation of a motion equation capable of being transformed into an equation of the same form as that of a heat conduction equation with respect to a term of a spatial temperature distribution and a term of a derivative of temperature with respect to time to perform a simulation of the heat conduction phenomenon of the simulation target, wherein in a case where a sign of a rate of temperature change of the simulation target and a sign of an acceleration of temperature change thereof are equal to each other, an attenuation coefficient of the motion equation is set to be smaller than an attenuation coefficient at a current time point, wherein in a case where the sign of the rate of temperature change of the simulation target and the sign of the acceleration of temperature change thereof are different from each other, the attenuation coefficient of the motion equation is restored to an original value calculated from the heat conduction equation, and a virtual mass which is a parameter corresponding to a mass in the motion equation is increased to be greater than a virtual mass at a current time point, and wherein when the virtual mass exceeds an upper limit value, the virtual mass is set to the upper limit value.

2. The computer program product according to claim 1, wherein an attenuation coefficient of the motion equation is set to a value smaller than an original value calculated from the heat conduction equation applied to the simulation target, or to zero to perform the numerical calculation of the motion equation.

3. The computer program product according to claim 2, wherein it is determined whether a condition for setting a rate of temperature change to zero is satisfied for each time pitch of the numerical calculation of the motion equation, and in a case where the condition is satisfied, the rate of temperature change is set to zero in the next time pitch of the numerical calculation of the motion equation.

4. The computer program product according to claim 2, further comprising:

computer code for determining whether a distribution of calculation values of temperatures obtained by the simulation of the heat conduction phenomenon reaches a steady state for each time pitch of the numerical calculation of the motion equation; and computer code for setting, in a case where it is determined that the distribution of the calculation values of the temperatures obtained by the simulation of the heat conduction phenomenon reaches the steady state, the attenuation coefficient of the motion equation to the original value calculated from the heat conduction equation applied to the simulation target to perform the numerical calculation of the motion equation.

5. The computer program product according to claim 1, wherein in a case where a sign of a rate of temperature change of the simulation target and a sign of an acceleration of temperature change thereof are equal to each other, an attenuation coefficient of the motion equation is set to be smaller than an attenuation coefficient at a current time point, wherein in a case where the sign of the rate of temperature change of the simulation target and the sign of the acceleration of temperature change thereof are different from each other, the attenuation coefficient of the motion equation is restored to an original value calculated from the heat conduction equation, and wherein when the number of time pitches from the start of the simulation becomes equal to or greater than a reference value, the attenuation coefficient of the motion equation is fixed to the original value calculated from the heat conduction equation.

6. A simulation apparatus that performs a coupled simulation of a structural-elastic phenomenon and a heat conduction phenomenon of a simulation target including a plurality of particles, comprising:
   a storage unit that stores a motion equation capable of being transformed into an equation of the same form as that of a heat conduction equation with respect to a term of a spatial temperature distribution and a term of a derivative of temperature with respect to time;
   a central processing unit that performs numerical calculation of the motion equation stored in the storage unit to calculate a temperature distribution of the simulation target; and
   an output unit that outputs a result of the numerical calculation performed by the central processing unit,
   wherein in a case where a sign of a rate of temperature change of the simulation target and a sign of an acceleration of temperature change thereof are equal to each other, an attenuation coefficient of the motion equation is set to be smaller than an attenuation coefficient at a current time point,
   wherein in a case where the sign of the rate of temperature change of the simulation target and the sign of the acceleration of temperature change thereof are different from each other, the attenuation coefficient of the motion equation is restored to an original value calculated from the heat conduction equation, and a virtual mass which is a parameter corresponding to a mass in the motion equation is increased to be greater than a virtual mass at a current time point, and
   wherein when the virtual mass exceeds an upper limit value, the virtual mass is set to the upper limit value.

7. The simulation apparatus according to claim 6,
wherein the motion equation includes an attenuation coefficient, and
wherein the central processing unit sets the attenuation coefficient of the motion equation to a value smaller than an original value calculated from the heat conduction equation applied to the simulation target, or to zero to perform the numerical calculation of the motion equation.

8. The simulation apparatus according to claim 7,
wherein the central processing unit determines whether a condition for setting a rate of temperature change to zero is satisfied for each time pitch of the numerical calculation of the motion equation, and sets, in a case where the condition is satisfied, the rate of temperature change to zero in the next time pitch of the numerical calculation of the motion equation.

9. The simulation apparatus according to claim 7,
wherein the central processing unit performs
determining whether a distribution of calculation values of temperatures calculated by the numerical calculation of the motion equation reaches a steady state for each time pitch of the numerical calculation of the motion equation, and
setting, in a case where it is determined that the distribution of the calculation values of the temperatures calculated by the numerical calculation of the motion equation reaches the steady state, the attenuation coefficient of the motion equation to the original value calculated from the heat conduction equation applied to the simulation target to perform the numerical calculation of the motion equation.

* * * * *